(12) United States Patent
Karbstein

(10) Patent No.: US 9,849,078 B2
(45) Date of Patent: Dec. 26, 2017

(54) PLANT EXTRACT FOR HAIR TONIC FOR TREATING BALDNESS AND PREVENTING HAIR LOSS AND HAIR BULB REGENERATOR

(71) Applicant: Franklin Kilbert Karbstein, Sao Paulo (BR)

(72) Inventor: Franklin Kilbert Karbstein, Sao Paulo (BR)

(*) Notice: Subject to any disclaimer, the term of this patent is extended or adjusted under 35 U.S.C. 154(b) by 109 days.

(21) Appl. No.: 14/662,953

(22) Filed: Mar. 19, 2015

(65) Prior Publication Data

US 2016/0271050 A1    Sep. 22, 2016

(51) Int. Cl.
- *A61K 36/00* (2006.01)
- *A61K 8/97* (2017.01)
- *A61Q 7/00* (2006.01)
- *A61K 8/34* (2006.01)

(52) U.S. Cl.
CPC .................. *A61K 8/97* (2013.01); *A61K 8/34* (2013.01); *A61Q 7/00* (2013.01)

(58) Field of Classification Search
CPC ...................................................... A61K 36/00
See application file for complete search history.

(56) References Cited

U.S. PATENT DOCUMENTS

2007/0122492 A1    5/2007    Behr et al.
2011/0311661 A1    12/2011   Behr et al.

FOREIGN PATENT DOCUMENTS

| CN | 1143476 A | * | 2/1997 | |
| CN | 104027257 A | * | 9/2014 | |
| EP | 2752183 A1 | * | 7/2014 | ............ A61K 36/11 |
| WO | 2014/184340 A1 | | 11/2014 | |

* cited by examiner

*Primary Examiner* — Qiuwen Mi
(74) *Attorney, Agent, or Firm* — Ernesto Garcia

(57) ABSTRACT

The present invention relates to an extract from *Pteridium Arachnoideum* or *Pteridium Aquilinum* and the preparation process thereof, useful for re-growing hair in subjects who have experienced hair loss due to any cause on head and eyebrow.

13 Claims, 8 Drawing Sheets

Figure 1:
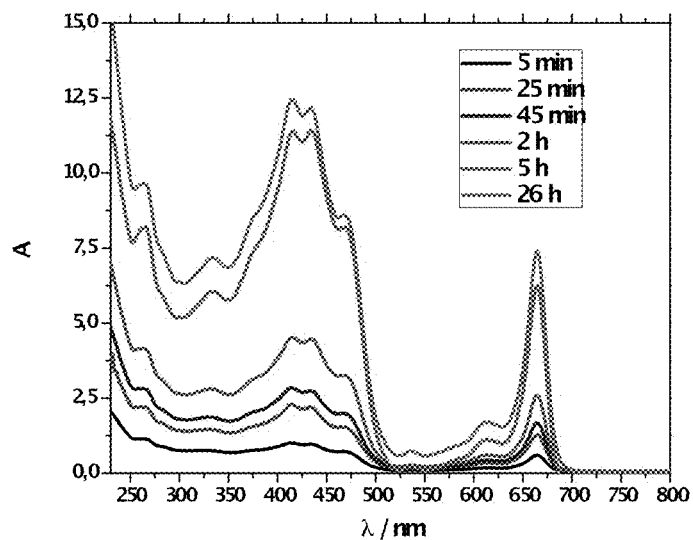

PLANT EXTRACT FOR HAIR TONIC FOR TREATING BALDNESS AND PREVENTING HAIR LOSS AND HAIR BULB REGENERATOR

FIELD OF THE INVENTION

The present invention relates to a potent hair tonic based on an extract of the plant *Pteridium Arachnoideum* or *Pteridium Aquilinum*, which strengthens the action of the hair follicles, increases the vitality of the tissues and strengthens the capillaries cells. The action and effect of this extract takes place in the first days of dermal application, and by the third day there is noticeable hair growth. The extract of *Pteridium Arachnoideum* or *Pteridium Aquilinum* strengthens the hair, increases the speed of growth, impedes or prevents hair loss, increases the size of the hair and increases the vitality of the hair bulb, reinvigorating it and causing the hair to sprout dormant bulbs.

BACKGROUND OF THE INVENTION

Healthy hair grows 0.5 to 1 centimeter per month. The cycle of birth, growth and shedding of the hair, usually lasts from 2 to 4 years. After the completion of its cycle, the hair bulb ruptures, giving off a layer of germ cells that will deposit on the papilla, generating a new hair bulb that, after three months, will reach the surface of the scalp. If the bulb does not give off the layer of germ cells, there is no hair formation [1].

There are many causes of hair loss. Alopecia androgenetic is a genetic cause of hair loss, which affects primarily men, but can also affect women. It is the atrophy of hair bulbs, due to dihydrotestosterone (DHT), a hormone produced by the interaction of testosterone with 5-alfa-reductase, resulting in shrinkage of the hair follicle, to its gradual disappearance. Researchers at the University of Pennsylvania, USA, found that in the bald area, the level of protein "prostaglandin D2 synthase" is very high [2], suggesting that this protein is also one of the causes of androgenetic alopecia. The researchers found that the prostaglandin may be a target for the treatment of male pattern baldness. Thence, it is possible to seek compounds that affect this receptor block and find out if baldness can be reversed or prevented.

There is another form of alopecia, Alopecia Areata, which is a disease of unknown cause that affects both men and women. It is characterized by a sudden loss of hair in the affected areas without alteration of the skin surface. Among the possible causes is a genetic predisposition that can be stimulated by triggers such as emotional stress and autoimmune diseases [3].

Other causes affect hair loss, such as thyroid dysfunction; hormonal problems; polycystic ovaries; autoimmune diseases; infectious or parasitic diseases; stress; extensive surgeries; medications; chemotherapy; radiation therapy; depression; dandruff; seborrhea; nutritional deficiencies; lack of protein; lack of vitamins and minerals in food; alcohol; as well as the natural cycle of hair life (about 2 to 4 years).

There are several treatments that include pharmaceuticals and cosmetics to promote hair re-growth and/or to prevent hair loss. Among some of the most common treatments in the market are: 1) Rogaine® (Minoxidil 2% or 5%) lotion, which is suitable for androgenetic alopecia. According to its Information Leaflet, they claim to see results in the stabilization of hair loss in three months of treatment. Its action is initiated in about the second month of application, however, the most significant results appear in the fourth month, and in other cases in the sixth or twelfth month of application. 2) Pantogar tablets (60 mg Calcium pantothenate, Cystine 20 mg, 60 mg thiamine nitrate, 100 mg medicinal yeast, Keratin 20 mg, aminobenzoic acid 20 mg). According to its Leaflet, it takes three to six months to ensure the effectiveness of treatment. 3) Propecia® (1 mg finasteride) tablets. It is contraindicated for women and children. Generally, the daily use in three months or more is necessary to notice the increasing hair growth or the diminishing of hair loss. Most important adverse reaction: decreased libido. 4) Low penetration LASER. Applied topically, stimulates the hair bulbs. Their result appears after 3 three months of treatment.

Therefore, the present invention offers faster and safer results than any of the current methods, to both men and women. It provides an effective treatment for the prevention of hair loss, the re-growth of hair despite the cause, the strengthening of hair strand and the revitalization of hair bulbs.

SUMMARY OF THE INVENTION

The purpose of this invention is to introduce a tonic to prevent hair loss in the scalp, eyebrows and body, as well as for the birth and growth of hair by using the extract of *Pteridium Arachnoideum* or *Pteridium Aquilinum*. The said extract stops hair loss in just a short period of time, enhancing hair growth and significantly increasing the size of the hair strand. Its effects begin in just three days.

The extract referred to in this invention also encourages the birth and growth of hair in the scalp, eyebrows, and body, where there is inactive hair bulb, but not where dead hair bulb exists, in any form or reason of alopecia, including androgenetic alopecia.

*Pteridium Arachnoideum* or *Pteridium Aquilinum* is also popularly known as "fern of taperas", "samambaia do campo", bracken, pluma grande.

The present invention also covers the method of obtaining the extract referred to in this invention. This invention is described in detail in the following sections.

BRIEF DESCRIPTION OF THE GRAPHICS

FIG. 1—Monitoring the extraction in ethanol by UV-Vis spectroscopy.

Figure 2:
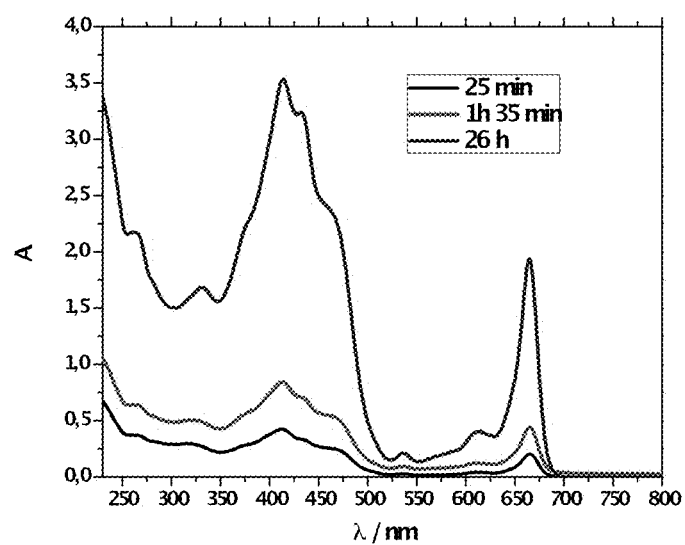

FIG. 2—Monitoring the extraction in isopropanol by UV-Vis spectroscopy.

Figure 3:
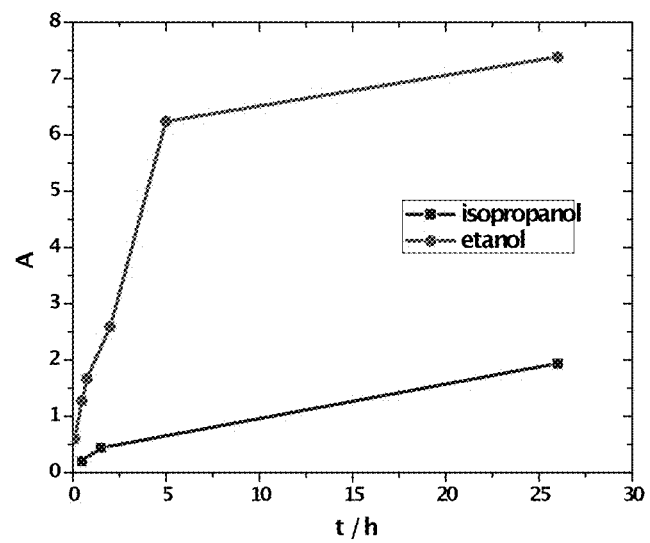

FIG. 3—Comparison of absorption versus time of extraction in ethanol and isopropanol.

Figure 4:
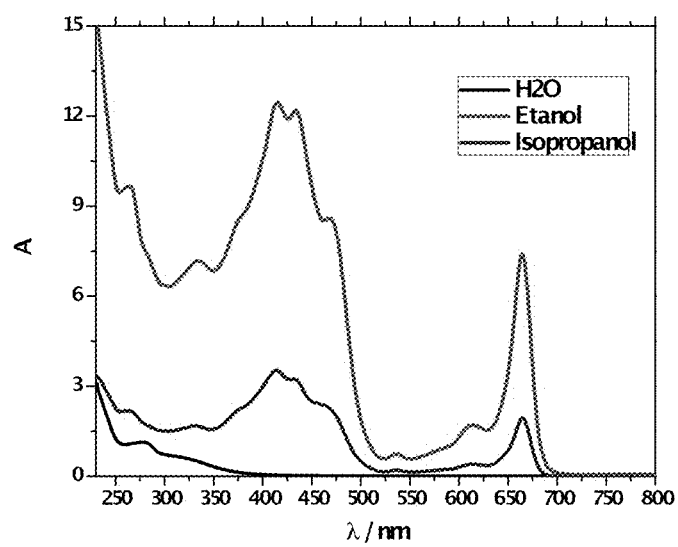

FIG. 4—Comparison of the spectra of absorption of the extracts in water, ethanol, and isopropanol after 26 hours of extraction.

Figure 5:
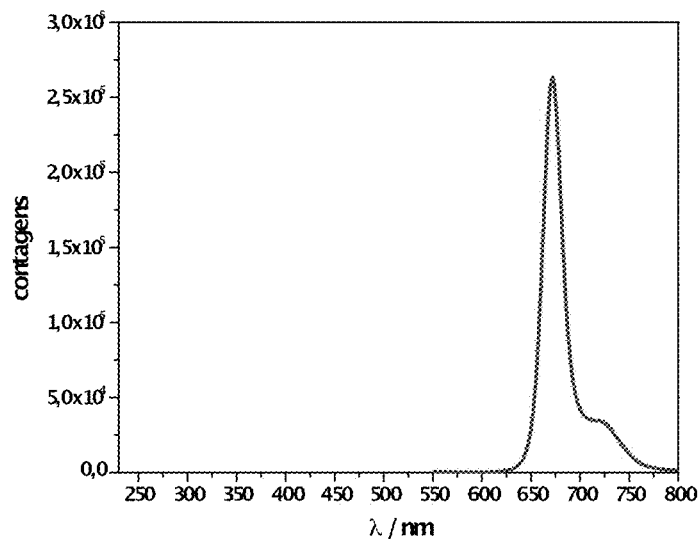

FIG. 5—Emission spectrum of the ethanol extract, $\lambda exc=365$ nm.

Figure 6:
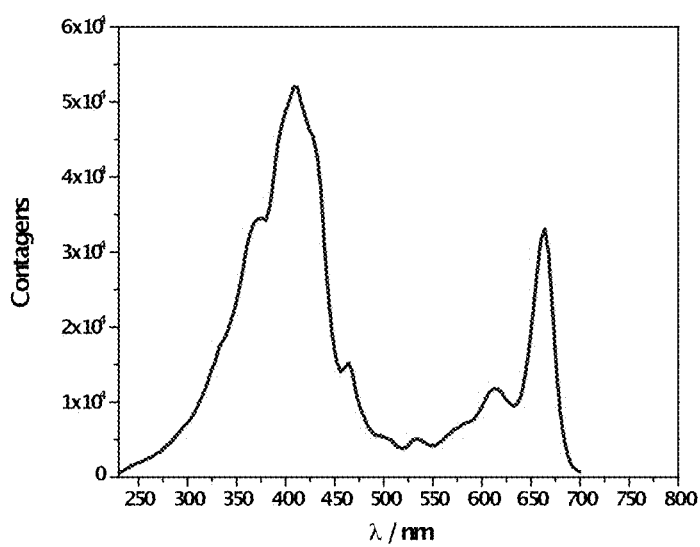

FIG. 6—Excitation spectrum of the ethanol extract, $\lambda emi=672$ nm.

Figure 7:

FIG. 7—Back of the subject's scalp (subject "A"), on the third day of treatment. It is observed the growth of new hair in sparse locations, new hair strand is strong and in natural color, brown (1 cm2 area on top of the skull: no hair strands).

Figure 8:
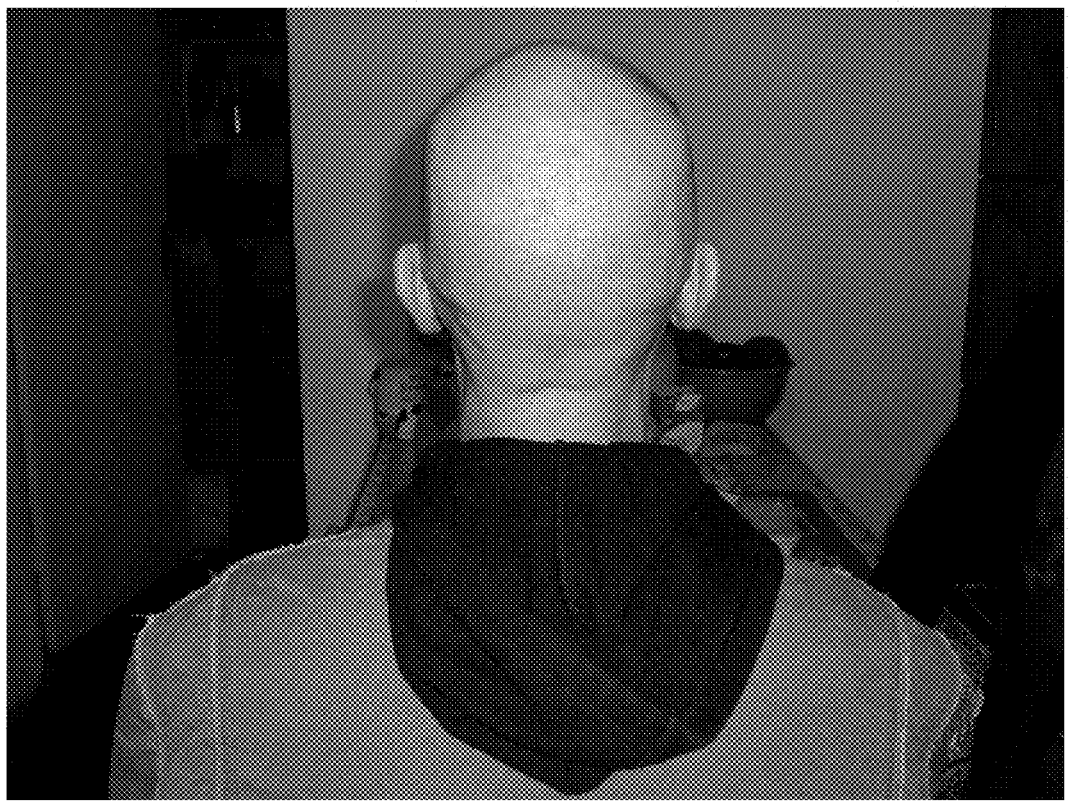

FIG. 8—Subject "A" within one week of treatment, showing the hair growth, increasing in caliber and, at the same time, noticing the appearance of new hair strands and formation of visible hair bulbs.

Figure 9:

FIG. 9—Subject "A" in one month of treatment, the hair strands begin to emerge throughout the treated, but still, rarefied area.

Figure 10:

FIG. 10—Subject "A" in three months of treatment (after skipping a month without applying the product, for the reason of the study), many hair strands have grown, packing more densely on the scalp, showing the presence of hair follicles in greater amount, to cover the bald area.

Figure 11:
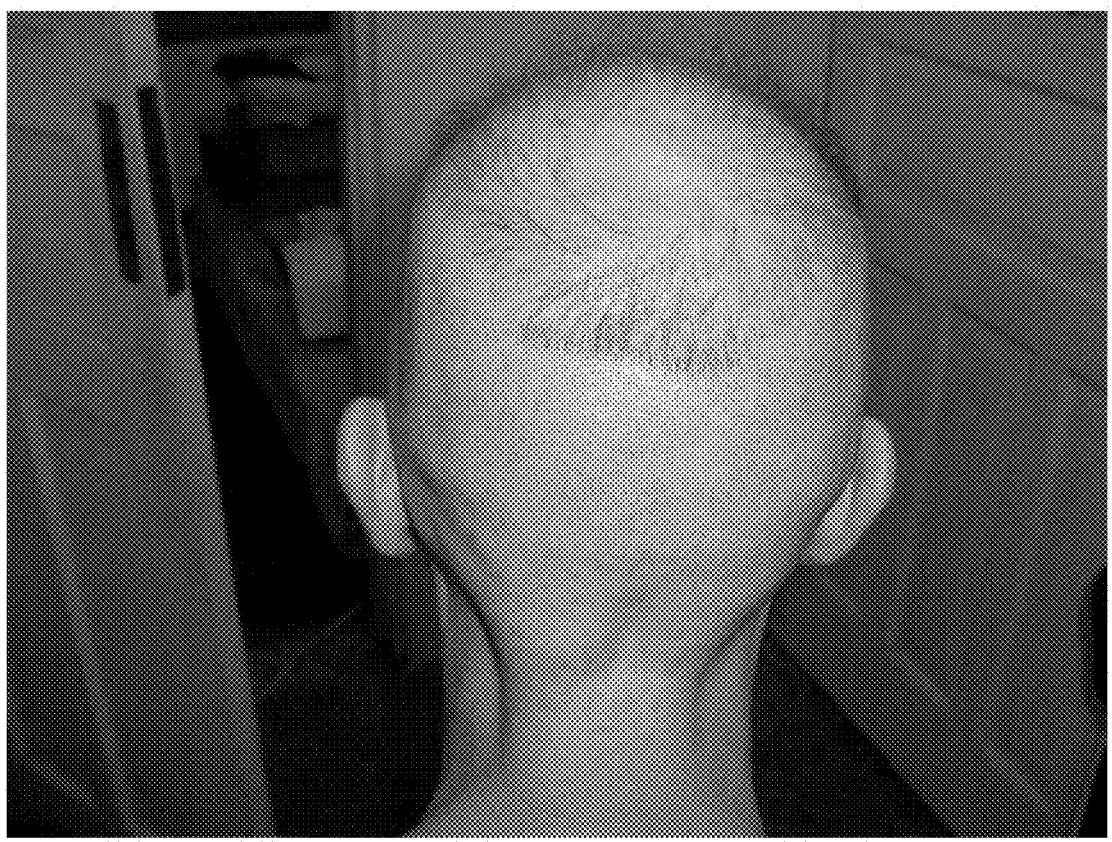

FIG. 11—Subject "A" within five months of treatment. One can notice the increasing growth and development of hair strands, in addition to its strengthening and concentration, virtually covering the entire bald area studied.

DETAILED DESCRIPTION OF THE INVENTION

The invention consists of the use of extract of *Pteridium Arachnoideum* or *Pteridium Aquilinum* as capillary tonic. The genus *Pteridium* contains a wide variety of chemical compounds, including tannins; shikimic, succinic and fumaric acids; pterosins; "pterosideos"; quercetin; prunasin; carotenoids; chlorophil and catecholamines. In particular, quercetin is a natural flavonoid having pharmacological properties such as anti-inflammatory, anticarcinogenic (because it acts on the immune system), antiviral, anti-histamine, anti-allergic, cardiovascular, it influences on the inhibition of cataracts in diabetics, among other benefits. High concentrations of quercetin are found in apples, onions, tea, broccoli and red wine. As for the catecholamines, they are chemical compounds derived from the amino acid tyrosine. Some of them are biogenic amines. The catecholamines are soluble in water and circulate in the blood 50% bound to plasma proteins. The most abundant catecholamines are adrenaline, noradrenalin and dopamine. As hormones, they are released by the adrenal gland during stress, such as psychological stress, or hypoglycemia. Regarding fumaric acid, recent studies have shown the efficacy of its derivatives in psoriasis.

The extract of *Pteridium Arachnoideum* or *Pteridium Aquilinum* was prepared as tonic and facilitator of hair growth. Its action occurs in the first days of dermal application. Experiments were conducted to better characterize its qualities. The tonic has promoted total stoppage of hair loss in men and women in one week, and hair growth has started from the third day of application. In all case studies, it was observed that its action is cumulative, preventing the fall of hair and stimulating the growth of new hair strand with daily treatment. The extract of *Pteridium Arachnoideum* or *Pteridium Aquilinum* encourages the maximum growth of the hair strands, increases hair strength, leads to the growth of hair strand where there is live bulb, and reverses the process of baldness in a short time. Experience shows that in people who had been bald for up to fifteen years, plenty of new hair growth occurred in a short period of time. In people who had been bald for more than fifteen years the process is slower, however, the action of this extract is observed in the activation of the hair bulbs, and the growth of thin hair follicles in a period of three months of treatment.

The action of this tonic also seems to indicate that it fights leucotricose, which is responsible for the loss of natural hair color by the lack of melanin production by the melanocyte cell.

Also reported were cases of disappearance of seborrhea with the use of the alcoholic extract of *Pteridium Arachnoideum* or *Pteridium Aquilinum*.

The objective of this invention is:

A—Using the extract of *Pteridium Arachnoideum* or *Pteridium Aquilinum* as hair tonic.

The advantages of this invention using the extract of *Pteridium Arachnoideum* or *Pteridium Aquilinum* are that it is the most potent and effective than any other product on the market; its action occurs rapidly and it is lasting, in all phases of hair growth, development and maintenance of hair cells and hair bulbs; it is natural, safe, painless, and easy to apply.

The present invention consists of:

a) Obtaining the hair tonic by extracting the active principle in a simple and quick way, without the need for many steps of synthesis and purification of synthetic dyes;

b) Utilizing *Pteridium Arachnoideum* or *Pteridium Aquilinum* as a natural species that naturally contains the active ingredient for the hair tonic.

Experimental Procedures

A—Preparation of Tonic by Extraction

In the beginning of the experimental procedures the leaves of *Pteridium* Arachnoideum or *Pteridium Aquilinum* were harvested, crushed and left to decoction in water, ethanol or isopropanol and then filtered.

FIGS. 1 and 2 show the evolution of the extraction of active principles in ethanol and isopropanol respectively, accompanied by an increase in visible light absorption of the extract with the extraction time. The electronic spectra show intense bands in the visible, typical of the chlorophyll absorption (maximum absorption at 667, 610, 538 and 413 nm), carotenoids (maximum absorption at 465 and 432 nm) [4] region. Bands in the ultraviolet region can be attributed to the electronic transitions of prunasin, present in fern. Although the prunasin plant has cyanogenic effect, mostly from fresh leaves and stem [5,6], there was no HCN gas evolution during the extraction, perhaps because of the use of dry leaves.

FIG. 3 is a comparison of the absorption of active ingredients regarding time and the two different solvents, being mostly evident the efficiency of the extraction in ethanol. Furthermore, we note that after 26 hours it already reaches constancy in the values of absorption, indicating that it is not necessary to go beyond this timeframe for the efficacy of the extraction.

FIG. 4 compares the absorption spectra of the extracts obtained with three different solvents, being, water, ethanol and isopropanol, after 26 hours of extraction, indicating that water is not able to extract carotenes or chlorophyll present in the plant, resulting in an electronic spectrum band without characteristics in the visible region.

In FIG. 5, the ethanol extract exhibits emission maximum at 672 nm, assigned to the emission of chlorophyll, and the corresponding excitation spectrum, in FIG. 6, is similar to the absorption spectrum of this species.

The pH of the extracts (water, 5.8; ethanol, 5.0; isopropanol, 5.7) is slightly acidic and viable for cutaneous use.

TLC chromatography of the ethanol extract solution using a 1:1 acetone:isopropanol showed three different spots: one of green color, related to chlorophyll, with an Rf=0.56 and two other colors developed using irradiation at 250 nm Rf equal to 0.67 and 0.90.

Mesoporous $TiO_2$ films were immersed in ethanol extract for 1 day. The $TiO_2$ acquired a pale greenish tinge, even with the solution acidified to pH 3, it was not possible to obtain the absorption spectrum in the visible. By removing these films from the solution, the adsorbed dye rapidly oxidizes, turning to beige color.

B—Application of the Tonic on the Scalp

The analysis of the action of the product makes us believe that most likely it acts in decreased androgen DHT, preventing the conversion of testosterone to DHT in the hair follicles of the scalp, in addition to other forms of action yet to be studied. However, it was observed a stoppage of hair loss in female subjects undergoing strong chemotherapy treatments, as well as growth and maintenance of hair, thus evidencing additional forms of action.

The extract effectively acts to induce hair growth, hair, and skin cells (capillary bulb) regeneration.

The extract has been proven effective for inducing the creation of hair cells, causing the hair bulbs to mature and sprout. In the case of subject "A" (Franklin Kilbert Karbstein), 50 years old, Caucasian, which is a carrier of androgenetic alopecia has been established for at least 25 years at the front area, and 15 years on the back and middle of the scalp, it was found both on the back and in the middle part, the hair grew again vigorously. The result of the action of the extract is evidenced from the 3rd third day of topical cutaneous application, FIG. 7. At this stage, the hair begins to emerge from active hair bulbs. From the third day, the action of the extract appears to be cumulative, and constantly induces the growth of new hair on the treated area, day after day, FIGS. 8, 9 and 10. By the fifth month of treatment, FIG. 11, the area of the scalp is filled almost entirely with hair. The hair strands grow stronger and noticeably better than the hair grown in the area where there was no treatment. The hair strands protrude vigorously up without bending during the first stage of growth, and then they start to bend with the continued growth and action of their weight on their base. The extract promotes the creation of new hair strands.

Method of Preparation

The method of producing the extract of *Pteridium Arachnoideum* or *Pteridium Aquilinum* consists of the following steps:

1. The green or dried leaves and/or stems of the plant *Pteridium Arachnoideum* or *Pteridium Aquilinum* may be used, duly crushed.
2. Place the plant *Pteridium Arachnoideum* or *Pteridium Aquilinum* in ethanol solution (which may be any type of ethanol, preferably ethanol 92%, or grain alcohol) and wait a minimum of 26 hours and maximum of 72 hours, when the extract with the active principles is already obtained.
3. The solution color is a deep green, almost like an olive green color.
4. The extract is then filtered, separating the pulp from the liquid.

The invention claimed is:

1. A composition base selected from the group consisting of creams, ointment, and emulsions, said composition base comprising an alcoholic extract from leaves, stems, roots or rhizomes of *Pteridium arachnoideum*, wherein the composition base containing from 1% to 99% of the extract by weight or volume.
2. The COMPOSITION BASE according to claim 1, in combination with a cosmetic.
3. The COMPOSITION BASE according to claim 1, in combination with a pharmaceutical product.
4. The COMPOSITION BASE according to claim 1, wherein the extract has a 92% alcohol content.
5. The COMPOSITION BASE according to claim 1, in combination with phytocosmetics.
6. The COMPOSITION BASE according to claim 1, in combination with soaps, shampoos, conditioners, hair gel, aerosol hair sprays, moisturizers, cream rinse, mousses, or oils.
7. The COMPOSITION BASE according to claim 1, in combination with topical pharmaceuticals.
8. The COMPOSITION BASE according to claim 1, in combination with aerosols, water in oil, or oil in water emulsions.
9. The COMPOSITION BASE according to claim 1, in combination with formulations containing hydroethanolic, ethanolic or oily extracts derived from natural sources or synthetic presentations containing any percentage of weight.
10. The COMPOSITION BASE according to claim 1, in combination with cosmetics, phytocosmetics, or topical pharmaceuticals containing from 1% to 99% of the extract by weight or volume.
11. The COMPOSITION BASE according to claim 1, in combination with cosmetics, phytocosmetics, or topical pharmaceutical products having formulations containing any percentage by weight.
12. The COMPOSITION BASE according to claim 1, in combination with cosmetics, phytocosmetics, or topical pharmaceutical products comprising formulations with tannins.
13. The COMPOSITION BASE according to claim 1, in combination with cosmetics, phytocosmetics, or topical pharmaceutical products having formulations associated with a drug, a vitamin, a salt, a sugar or any excipient in any percentage.

* * * * *